ns Patent [19]

Roll

[11] 4,035,373
[45] July 12, 1977

[54] PREPARATION OF PIPERIDINYL-ALKYL-BENZAMIDES
[75] Inventor: William D. Roll, Toledo, Ohio
[73] Assignee: The University of Toledo, Toledo, Ohio
[21] Appl. No.: 660,652
[22] Filed: Feb. 23, 1976
[51] Int. Cl.² .................................... C07D 211/36
[52] U.S. Cl. ................ 260/293.77; 260/295 AM; 424/267
[58] Field of Search ............................. 260/293.77
[56] References Cited
U.S. PATENT DOCUMENTS

| 3,342,826 | 9/1967 | Miller et al. | 260/293.77 |
|---|---|---|---|
| 3,532,704 | 10/1970 | Suter et al. | 260/293.77 |
| 3,862,139 | 1/1975 | Podesva et al. | 260/293.77 |
| 3,891,671 | 6/1975 | Thominet | 260/293.77 |

Primary Examiner—Norma S. Milestone
Attorney, Agent, or Firm—John C. Purdue

[57] ABSTRACT

New piperidinyl-alkyl-benzamides and salts thereof are disclosed, together with a method for the production of the benzamides and salts. The benzamides, which have beta-adrenergic agonist effects, have the general formula

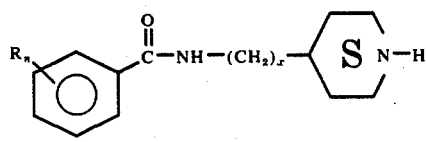

Formula I The hydrochlorides which exemplify the salts, have the general formula

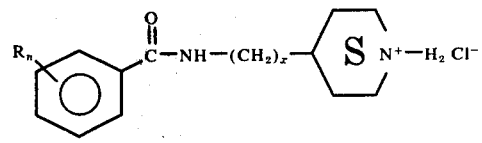

In the foregoing formulas R is hydrogen, an alkyl group having from 1 to 4 carbon atoms, an alkoxy group having from 1 to 4 carbon atoms, halo, amino, hydroxy or trifluoromethyl, $n$ is 1, 2 or 3 when R is methoxy but is otherwise 1, and $x$ is 1, 2 or 3. The hydrochloride salts of the benzamides according to the invention can be produced by the reactions illustrated below:

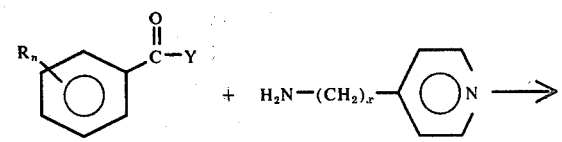

Formula II                Formula III

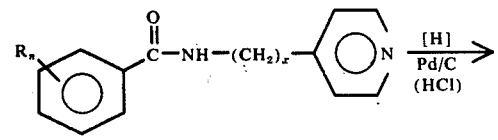

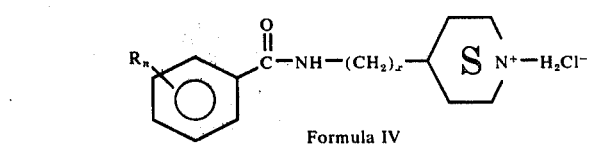

Formula IV

Wherein R, $n$ and $x$ have the meanings set forth above and Y can be —Cl, —F, or —OCH₃.

5 Claims, No Drawings

PREPARATION OF PIPERIDINYL-ALKYL-BENZAMIDES

BACKGROUND OF THE INVENTION

Numerous substituted benzamides have been suggested*. So far as is known, the substituted piperidinylalkyl-benzamides represented by the foregoing formula are new, and beta-adrenergic agonist effects in any substituted benzamide are also new.

*See, for example the following U.S. Pats. Nos.: 3,704,322; 3,719,687; 3,706,750; 3,647,804; 3,631,102; 3,634,511; 3,644,644; 3,504,028; 3,432,549; 3,342,679; 3,751,464; 3,660,461; 3,808,315; 3,825,595; 3,830,932; 3,885,040; and 3,879,540.

DESCRIPTION OF THE PREFERRED EMBODIMENTS

Example 1, below, illustrates the production of piperidinyl-alkyl-benzamides of the instant invention.

EXAMPLE 1

A 250 ml. round bottom flask was used to produce N-(4-pyridylmethyl)-m-trifluoromethylbenzamide from 0.12 mole m-trifluoromethyl benzoyl fluoride and 0.12 mole 4-pyridylmethyl amine in 0.122 mole triethylamine and 75 ml. chloroform. The 4-pyridylmethyl amine, the triethyl amine and the chloroform were charged to the flask, and the m-trifluoromethyl benzoyl fluoride was then added gradually in a period of about 30 minutes. The contents of the flask were stirred effectively during the addition of the m-trifluoromethyl benzoyl fluoride and for about thirty minutes after that addition was complete. The reaction temperature was approximately 10°–15° C. Solids were separated from the reaction mixture by filtration, and following removal of the solvent in vacuo, the crude N-(4-pyridylmethyl)-m-trifluoromethylbenzamide was recovered by filtration and purified by recrystallization from aqueous ethanol. The total yield of purified N-(4-pyridylmethyl)-m-trifluoromethylbenzamide, melting point 81° C., was 29.0 g., 86.3 percent of theory.

** The term mole is used herein to refer to gram mole.

Conversion of the intermediate pyridylmethylbenzamide derivative to its corresponding piperidine analog was achieved by catalytic hydrogenation. The pyridyl analog (0.04) mole was dissolved in 75 ml. of absolute ethanol containing concentrated HCl (0.041 mole) and 1.1 g. 10% Pd/C and reduced using an initial pressure of 68 psi. $H_2$ at a temperature of 60°–70° C. After 5 hours, the reduction was complete; the catalyst was filtered off and the solvent removed in vacuo to obtain the crude N-(4piperidinylmethyl)-m-trifluoromethylbenzamide hydrochloride. Recrystallization from isopropanol gave the pure product, 12.06 g., 93.5 percent of theory, melting point 152° C.

EXAMPLES 2–12

Other benzamides according to the invention, and having the structure represented by Formula I, above, have been produced by the method described in Example 1. In each case, an equivalent amount of a substituted benzoyl halide or ester having a structure represented by Formula II, above, was substituted for the m-trifluoromethyl benzoyl fluoride, and was reacted with a 4-pyridylalkyl amine, Formula III, above, by the procedure described in Example 1. The value of $n$ and the identity and position of R, Formula I and Formula II, and the numerical value of $x$, Formula I, Formula III and Formula IV, for these several preparations, and the melting point of the final benzamide hydrochloride, are given in Table I, below:

Table I

| Example | R Identity | R Position | n | x | Melting point ° C. benzamide hydrochloride |
|---|---|---|---|---|---|
| 2 | —H |  | 1 | 1 | 176.7 |
| 3 | —$CH_3$ | p- | 1 | 1 | 226.6 |
| 4 | —$CH_3$ | o- | 1 | 1 | 223 |
| 5 | —$OCH_3$ | p- | 1 | 1 | 267 |
| 6 | —OCH | 3,4,5- | 3 | 1 | 229.8 |
| 7 | —Cl | p- | 1 | 1 | 180.1 |
| 8 | —$NH_2$ | p- | 1 | 1 | 189 (Di-HCl) |
| 9 | —OH | p- | 1 | 1 | 213 |
| 10 | —F | p- | 1 | 1 | 170.2 |
| 11 | —$OCH_3$ | 3,4,5- | 3 | 2 | 193.8 |
| 12 | —$OCH_3$ | 3,4,5- | 3 | 3 | 147.5 |

Structures of the several compounds, after purification, were verified by means of an infrared spectrophotometer, an NMR spectrophotometer, a mass spectrometer and by elemental analyses for carbon and hydrogen. The carbon and hydrogen analyses, in all instances, equaled the theoretical value, plus or minus 0.4 percent.

The intermediate pyridylalkylbenzamides produced, Examples 2–12, are represented by Formula IV where the identity and position of R and the values of $n$ and $x$ are the same as in Table I for each of the Examples. The melting point of each pyridylmethylbenzamide intermediate is given in Table II, below:

Table II

| Example | Melting Point ° C., Formula IV |
|---|---|
| 2 | 119 |
| 3 | 142 |
| 4 | 143 |
| 5 | 143.3 |
| 6 | 167.6 |
| 7 | 116.8 |
| 8 | 201.4 |
| 9 | 170 |
| 10 | 60.8 |
| 11 | 131 |
| 12 | 87 |

The pyridylalkylbenzamides are believed to be new compounds. They have the general formula

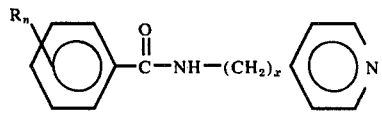

where R, $n$ and $x$ have the meanings set forth above. The pyridylalkylbenzamides are useful as intermediates for the production of piperidinyl-alkyl-benzamides of the invention by the chemistry set forth in Example 1.

The other substituted piperidinyl-alkyl-benzamides and pyridyl-alkyl-benzamides according to the invention, in addition to those specifically produced as described in Examples 1–12, can be produced by the procedure described in Example 1, with appropriate substitution of equivalent amounts of other benzoyl halides or esters, Formula II, of equivalent amounts of other 4-pyridyl alkyl amines, Formula III, or of both. It has also been found that substituted piperidinyl-alkyl-benzamides according to the invention, Formula I, can be produced by the procedure described in Example 1, except that an equal volume of dimethylacetamide is substituted for the chloroform. The procedure is the same as that described, except that, after solids are removed from the reaction mixture by filtration, the crude benzamide product is precipitated from the filtrate by the addition of distilled water.

Test Procedures Used to Demonstrate Beta-Adrenergic Agonist Activity for Substituted Piperidinyl-Alkyl-Benzamides According to the Invention, Formula I In Vitro Activity on the Isolated Rat Uterus, Rat Ileum and Guinea Pig Ileum Adult rats and young guinea pigs of either sex were sacrificed by a blow to the back of the head (rats) or carbon dioxide asphyxiation (guinea pigs). Strips of uterus and ileum approximately 1 cm.in length were immediately excised and suspended in a Magnus bath apparatus of volume 75 cc. which was maintained at 37° C. and through which air was constantly bubbled. The rat ileum and uterus strips were incubated in Locke-Ringer's solution and the guinea pig ileum strips in Tyrode's solution. Tissue strips were washed between drugs by draining the bath and immediately replacing with the appropriate fresh solution warmed to 37° C. Spontaneous motility was recorded by a Beckman type R-411 dynograph and strip chart recorder. Drugs were added to the bath as indicated.

In Vitro Activity on the Isolated Guinea Pig Tracheal Chain

Young guinea pigs of either sex were sacrificed by carbon dioxide administration. The trachea was immediately isolated and excised. It was incubated in Ringer's solution while being cut into 10 rings of approximately equal width which were then connected by short loops of silk thread*. The chain was then suspended in a Magnus bath containing 75 cc. of Van Dyke - Hastings solution to which 0.05 percent dextrose had been added. The bath was maintained at 37° C. and constantly aerated. The chain was washed between drugs as described above. Very little tension was placed on the chain and its spontaneous contractions were recorded on a dynograph and strip chart recorder, also. Reactivity of the chain was assured by monitoring its response to sequential additions of isoproterenol HCl (Isuprel HCl solution) 0.1 percent** and histamine dihydrochloride solution 0.1 percent.

* The technique is described by Castillo and de Beer, J. Pharmacol. Exptl. Therap. 90, 104 (1947).
** The terms "percent" and "parts" are used herein, and in the appended claims, to refer to percent and parts by weight, unless otherwise indicated.

Blood Pressure and Heart Rate in Anesthetized Rats

Adult rats weighing 0.29–0.38 kg. were anesthetized by i.p.

* injection of a 25 percent aqueous urethane solution at a dosage level of 1.2 gm/kg of urethane based on body weight. Heart rate was recorded by a Beckman type R-411 dynograph and strip chart recorder by means of three electrodes inserted s.c. ** at the right chest, left chest, and left lower abdomen of the animal. Blood pressure was determined by direct carotid artery cannulation and was recorded by means of a mercury manometer and muscle lever tracing on a kymograph. Drugs were injected i.p. at intervals no shorter than 5 minutes.

*** intra peritoneal.
**** subcutaneous.

The Test Results With N-(4-piperidinylmethyl)-m-trifluoromethylbenzamide hydrochloride, Used Both as a Methanol Solution and as the Hydrochloride Salt in 3 Percent Aqueous Solution Results of Testing for in Vitro Activity on the Isolated Rat Uterus, Rat Ileum and Guinea Pig Ileum A dose of 0.2 cc. N-(4-piperidinylmethyl)-m-trifluoromethylbenzamide hydrochloride (0.1 percent aqueous solution) caused a 65 percent decrease in amplitude of the rat uterine contractions and also a decreased frequency of contraction. A dose of 0.3 cc. of the same concentration caused complete relaxation of the uterus after 3 minutes, recovery of contractions beginning 35 minutes after dosing.

By way of comparison, it was determined that an isoproterenol hydrochloride solution (0.1 percent) in water, at a 0.1 ml. dosage, caused immediated relaxation of the uterus, recovery beginning in 9 minutes.

A 0.2 cc. dosage of N-piperidinylmethyl)-m-trifluoromethylbenzamide hydrochloride solution (0.1 percent) decreased the amplitude and frequency of contractions of the rat ileum, but did not relax the tissue completely. Both isoproterenol hydrochloride (0.1 percent solution in water: 0.1 cc. dosage) and epinephrine hydrochloride solution (0.1 percent in water: 0.05 cc. dosage) caused relaxation of the rat ileum.

An aqueous solution of N-(4-piperidnylmethyl)-m-trifluoromethylbenzamide hydrochloride (0.1 percent: dosage 0.2 cc.) antagonized the effect of an acetylcholine chloride solution in distilled water (0.1 percent: 0.1 cc. dosage) on the rat ileum. Atropine can also be used to antagonize the effect of the acetylcholine chloride solution, but atropine, alone, has no relaxant effect on this tissue. Isoproterenol antagonizes the effect of acetylcholine chloride solution on the rat ileum and, as indicated above, also has a relaxant effect.

An aqueous solution of N-(4-piperidinylmethyl-m-trifluoromethylbenzamide hydrochloride (0.1 percent: dosage 0.2 cc.) caused a relaxant effect on guinea pig ileum; this dose also antagonized the stimulant effect of a serotonin creatinine sulfate monohydrate solution in distilled water (0.1 percent: dosage 0.05 cc.) and of a histamine dihydrochloride solution in distilled water (0.1 percent: dosage 0.05 cc.).

Results of Testing for in Vitro Activity on the Isolated Guinea Pig Trachael Chain An aqueous solution of N-(4-piperidinylmethyl)-m-trifluoromethylbenzamide hydrochloride (0.05 percent: 0.1 cc. dosage) was effective to cause relaxation of the trachael chain. The chain also responded, with relaxation, to an isoproterenol hydrochloride solution in distilled water (0.1 percent: dosage 0.1 cc.).

Results of Testing for Blood Pressure and Heart Rate in Anesthetized Rats

A dose of 2 mg/kg of a 0.5 percent aqueous solution of N-(4-piperidinylmethyl)-m:trifluromethylbenzamide hydrochloride caused a slow fall in blood pressure after seven minutes, while a dosage of 1 mg/kg of a 0.05 percent solution of N-(4-piperidinylmethyl)-m:trifluoromethylbenzamide hydrochloride caused no change in blood pressure and a 2 mg/kg dosage of a 0.05 percent solution of N-(4-piperidinylmethyl)-m-grifluoromethylbenzamide hydrochloride caused a slight, sustained rist in blood pressure. By way of comparison, a dosage on only 0.5 mg/kg of a 0.1 percent solution in distilled water of isoproterenol hydrochloride caused a precipitous fall in blood pressure, increased the heart rate, and caused heart beat irregularities.

It was determined, in all cases, that the solvents used in performing the tests described above had no effect along on any of the tissues or functions monitored.

The results reported above shown that N-(4-piperidinylmethyl)-m-trifluoromethylbenzamide hydrocholride has betaadrenergic agonist effects, but does not have alpha adrenergic agonist effects. They show it to be as effective in its beta adrenergic agonist effects as the most effective previously known compound, namely, isoproterenol hydrochloride, but to have only a minor, and controllable, effect on blood pressure. This makes the compound a peculiarly advantageous beta adrenergic agonist.

The other compounds according to the present invention, Formula I, which have been synthesized, Examples 2–12 have also been found to be acitve as beta adrenergic agonists. Those compounds where the R substituent is in the meta or para position are preferred, including N-(4-piperidinyl-methyl)-3,4,5-trimethoxybenzamide hydrochloride. The hydrochloride salts are preferred because they are prepared easily by the chemistry described above, but other physiologically acceptable salts can also be produced by reacting the benzamide with the appropriate acid. Examples of physiologically acceptable salts other than the hydrochlorides include the citrates, tartrates, sulfates and hydrobromides.

I claim:

1. Piperidinyl-alkyl-benzamides having the general formula

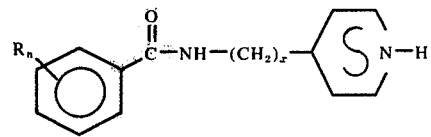

Formula I wherein R is hydrogen, an alkyl group having from 1 to 4 carbon atoms, an alkoxy group having from 1 to 4 carbon atoms, halo, amino, hydroxy or, where R is meta, trifluoromethyl, $n$ is 1, 2 or 3 when R is methoxy, but is otherwise 1, and $x$ is 1, 2 or 3, with the proviso that when $n$ is 1, R in the meta position is trifluoromethyl or hydrogen, and physiologically acceptable salts thereof.

2. Piperidinyl-alkyl-benzamides as claimed in claim 1 wherein the R substituent is trifluoromethyl in the meta position.

3. Piperidinyl-alkyl-benzamides as claimed in claim 1 wherein the R substituent is in the para position.

4. Piperidinyl-alkyl-benzamides as claimed in claim 1 wherein the R substituent is 3,4,5-trimethoxy.

5. The piperidinyl-alkyl-benzamide claimed in claim 4 wherein $x$ is 1.

* * * * *